United States Patent
Carlton et al.

(10) Patent No.: US 9,603,652 B2
(45) Date of Patent: Mar. 28, 2017

(54) ELECTROSURGICAL INSTRUMENT INCLUDING A SENSOR

(75) Inventors: John D. Carlton, Las Vegas, NV (US); Darren Odom, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 1638 days.

(21) Appl. No.: 12/195,624

(22) Filed: Aug. 21, 2008

(65) Prior Publication Data

US 2010/0049187 A1 Feb. 25, 2010

(51) Int. Cl.
| | |
|---|---|
| *A61B 18/14* | (2006.01) |
| *A61B 18/12* | (2006.01) |
| *A61B 5/00* | (2006.01) |
| *A61B 17/00* | (2006.01) |
| *A61B 18/00* | (2006.01) |

(52) U.S. Cl.
CPC ........ *A61B 18/1206* (2013.01); *A61B 5/0059* (2013.01); *A61B 18/1442* (2013.01); *A61B 5/0008* (2013.01); *A61B 18/1445* (2013.01); *A61B 2017/00057* (2013.01); *A61B 2018/00702* (2013.01); *A61B 2018/00791* (2013.01)

(58) Field of Classification Search
CPC ............ A61B 18/1233; A61B 18/1442; A61B 18/1445; A61B 18/1447; A61B 2018/00577; A61B 2018/00589; A61B 2018/00595; A61B 2018/00601; A61B 2018/00607; A61B 2018/0063; A61B 2018/00642; A61B 2018/00666; A61B 2018/00702; A61B 2018/00791; A61B 2018/126; A61B 2018/146; A61B 2017/00057; A61B 5/0059

USPC ... 606/38, 42, 52, 41; 607/98–100, 102, 115
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Thomas Giuliani

(57) ABSTRACT

An electrosurgical system includes an electrosurgical generator, an electrosurgical instrument, an optical clarity sensor and a control component. The electrosurgical generator generates electrosurgical energy for use during electrosurgery. The electrosurgical instrument is coupled to the electrosurgical generator and treats tissue. The optical clarity sensor is coupled to the electrosurgical generator and is adapted to measure tissue with at least two optical frequencies. The control component is operatively coupled to the optical clarity sensor and receives sensor data therefrom. The control component communicates control instructions to the electrosurgical generator to control the generation of the electrosurgical energy.

12 Claims, 2 Drawing Sheets

(56) References Cited

U.S. PATENT DOCUMENTS

| | | |
|---|---|---|
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,805,623 A * | 2/1989 | Jobsis ............... A61B 5/14551 250/339.12 |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |

(56) References Cited

U.S. PATENT DOCUMENTS

| | | | |
|---|---|---|---|
| 5,356,408 | A | 10/1994 | Rydell |
| 5,366,477 | A | 11/1994 | LeMarie, III et al. |
| 5,368,600 | A | 11/1994 | Failla et al. |
| 5,374,277 | A | 12/1994 | Hassler |
| 5,376,089 | A | 12/1994 | Smith |
| 5,383,875 | A | 1/1995 | Bays et al. |
| 5,383,897 | A | 1/1995 | Wholey |
| 5,389,098 | A | 2/1995 | Tsuruta et al. |
| 5,389,103 | A | 2/1995 | Melzer et al. |
| 5,389,104 | A | 2/1995 | Hahnen et al. |
| 5,391,166 | A | 2/1995 | Eggers |
| 5,391,183 | A | 2/1995 | Janzen et al. |
| 5,396,900 | A | 3/1995 | Slater et al. |
| 5,403,312 | A | 4/1995 | Yates et al. |
| 5,403,342 | A | 4/1995 | Tovey et al. |
| 5,405,344 | A | 4/1995 | Williamson et al. |
| 5,409,763 | A | 4/1995 | Serizawa et al. |
| 5,411,519 | A | 5/1995 | Tovey et al. |
| 5,411,520 | A | 5/1995 | Nash et al. |
| 5,413,571 | A | 5/1995 | Katsaros et al. |
| 5,415,656 | A | 5/1995 | Tihon et al. |
| 5,415,657 | A | 5/1995 | Taymor-Luria |
| 5,422,567 | A | 6/1995 | Matsunaga |
| 5,423,810 | A | 6/1995 | Goble et al. |
| 5,425,690 | A | 6/1995 | Chang |
| 5,425,739 | A | 6/1995 | Jessen |
| 5,429,616 | A | 7/1995 | Schaffer |
| 5,431,672 | A | 7/1995 | Cote et al. |
| 5,431,674 | A | 7/1995 | Basile et al. |
| 5,437,292 | A | 8/1995 | Kipshidze et al. |
| 5,438,302 | A | 8/1995 | Goble |
| 5,439,478 | A | 8/1995 | Palmer |
| 5,441,517 | A | 8/1995 | Kensey et al. |
| 5,443,463 | A | 8/1995 | Stern et al. |
| 5,443,464 | A | 8/1995 | Russell et al. |
| 5,443,480 | A | 8/1995 | Jacobs et al. |
| 5,445,638 | A | 8/1995 | Rydell et al. |
| 5,445,658 | A | 8/1995 | Durrfeld et al. |
| 5,449,480 | A | 9/1995 | Kuriya et al. |
| 5,451,224 | A | 9/1995 | Goble et al. |
| 5,454,823 | A | 10/1995 | Richardson et al. |
| 5,454,827 | A | 10/1995 | Aust et al. |
| 5,456,684 | A | 10/1995 | Schmidt et al. |
| 5,458,598 | A | 10/1995 | Feinberg et al. |
| 5,460,629 | A | 10/1995 | Shlain et al. |
| 5,461,765 | A | 10/1995 | Linden et al. |
| 5,462,546 | A | 10/1995 | Rydell |
| 5,472,442 | A | 12/1995 | Klicek |
| 5,472,443 | A | 12/1995 | Cordis et al. |
| 5,478,351 | A | 12/1995 | Meade et al. |
| 5,480,406 | A | 1/1996 | Nolan et al. |
| 5,480,409 | A | 1/1996 | Riza |
| 5,484,436 | A | 1/1996 | Eggers et al. |
| 5,496,312 | A | 3/1996 | Klicek |
| 5,496,317 | A | 3/1996 | Goble et al. |
| 5,496,347 | A | 3/1996 | Hashiguchi et al. |
| 5,499,997 | A | 3/1996 | Sharpe et al. |
| 5,509,922 | A | 4/1996 | Aranyi et al. |
| 5,512,721 | A | 4/1996 | Young et al. |
| 5,514,134 | A | 5/1996 | Rydell et al. |
| 5,527,313 | A | 6/1996 | Scott et al. |
| 5,528,833 | A | 6/1996 | Sakuma |
| 5,529,067 | A | 6/1996 | Larsen et al. |
| 5,531,744 | A | 7/1996 | Nardella et al. |
| 5,536,251 | A | 7/1996 | Evard et al. |
| 5,540,684 | A | 7/1996 | Hassler, Jr. |
| 5,540,685 | A | 7/1996 | Parins et al. |
| 5,540,706 | A | 7/1996 | Aust et al. |
| 5,540,715 | A | 7/1996 | Katsaros et al. |
| 5,542,945 | A | 8/1996 | Fritzsch |
| 5,558,671 | A | 9/1996 | Yates |
| 5,558,672 | A | 9/1996 | Edwards et al. |
| 5,562,619 | A | 10/1996 | Mirarchi et al. |
| 5,562,699 | A | 10/1996 | Heimberger et al. |
| 5,562,720 | A | 10/1996 | Stern et al. |
| 5,564,615 | A | 10/1996 | Bishop et al. |
| 5,569,241 | A | 10/1996 | Edwardds |
| 5,569,243 | A | 10/1996 | Kortenbach et al. |
| 5,571,100 | A | 11/1996 | Goble et al. |
| 5,573,424 | A | 11/1996 | Poppe |
| 5,573,534 | A | 11/1996 | Stone |
| 5,573,535 | A | 11/1996 | Viklund |
| 5,575,799 | A | 11/1996 | Bolanos et al. |
| 5,575,805 | A | 11/1996 | Li |
| 5,578,052 | A | 11/1996 | Koros et al. |
| 5,579,781 | A | 12/1996 | Cooke |
| 5,582,611 | A | 12/1996 | Tsukagoshi et al. |
| 5,582,617 | A | 12/1996 | Klieman et al. |
| 5,585,896 | A | 12/1996 | Yamazaki et al. |
| 5,590,570 | A | 1/1997 | LeMaire, III et al. |
| 5,591,181 | A | 1/1997 | Stone et al. |
| 5,597,107 | A | 1/1997 | Knodel et al. |
| 5,601,224 | A | 2/1997 | Bishop et al. |
| 5,601,601 | A | 2/1997 | Tal et al. |
| 5,601,641 | A | 2/1997 | Stephens |
| 5,603,711 | A | 2/1997 | Parins et al. |
| 5,603,723 | A | 2/1997 | Aranyi et al. |
| 5,611,798 | A | 3/1997 | Eggers |
| 5,611,808 | A | 3/1997 | Hossain et al. |
| 5,611,813 | A | 3/1997 | Lichtman |
| 5,620,415 | A | 4/1997 | Lucey et al. |
| 5,620,453 | A | 4/1997 | Nallakrishnan |
| 5,620,459 | A | 4/1997 | Lichtman |
| 5,624,452 | A | 4/1997 | Yates |
| 5,626,578 | A | 5/1997 | Tihon |
| 5,626,609 | A | 5/1997 | Zvenyatsky et al. |
| 5,630,833 | A | 5/1997 | Katsaros et al. |
| 5,637,110 | A | 6/1997 | Pennybacker et al. |
| 5,638,003 | A | 6/1997 | Hall |
| 5,643,294 | A | 7/1997 | Tovey et al. |
| 5,647,869 | A | 7/1997 | Goble et al. |
| 5,647,871 | A | 7/1997 | Levine et al. |
| 5,649,959 | A | 7/1997 | Hannam et al. |
| 5,655,650 | A | 8/1997 | Naitou |
| 5,658,281 | A | 8/1997 | Heard |
| D384,413 | S | 9/1997 | Zlock et al. |
| 5,662,667 | A | 9/1997 | Knodel |
| 5,665,100 | A | 9/1997 | Yoon |
| 5,667,526 | A | 9/1997 | Levin |
| 5,674,220 | A | 10/1997 | Fox et al. |
| 5,674,229 | A | 10/1997 | Tovey et al. |
| 5,681,282 | A | 10/1997 | Eggers et al. |
| 5,688,270 | A | 11/1997 | Yates et al. |
| 5,690,652 | A | 11/1997 | Wurster et al. |
| 5,690,653 | A | 11/1997 | Richardson et al. |
| 5,693,051 | A | 12/1997 | Schulze et al. |
| 5,693,920 | A | 12/1997 | Maeda |
| 5,695,522 | A | 12/1997 | LeMaire, III et al. |
| 5,700,261 | A | 12/1997 | Brinkerhoff |
| 5,700,270 | A | 12/1997 | Peyser et al. |
| 5,702,390 | A | 12/1997 | Austin et al. |
| 5,707,369 | A | 1/1998 | Vaitekunas et al. |
| 5,709,680 | A | 1/1998 | Yates et al. |
| 5,716,366 | A | 2/1998 | Yates |
| 5,720,744 | A | 2/1998 | Eggleston et al. |
| 5,722,421 | A | 3/1998 | Francese et al. |
| 5,725,536 | A | 3/1998 | Oberlin et al. |
| 5,727,428 | A | 3/1998 | LeMaire, III et al. |
| 5,735,848 | A | 4/1998 | Yates et al. |
| 5,743,906 | A | 4/1998 | Parins et al. |
| 5,752,973 | A | 5/1998 | Kieturakis |
| 5,755,717 | A | 5/1998 | Yates et al. |
| 5,759,188 | A | 6/1998 | Yoon |
| 5,762,609 | A * | 6/1998 | Benaron ............ G01N 21/4795 600/473 |
| 5,766,130 | A | 6/1998 | Selmonosky |
| 5,766,166 | A | 6/1998 | Hooven |
| 5,766,170 | A | 6/1998 | Eggers |
| 5,766,196 | A | 6/1998 | Griffiths |
| 5,769,849 | A | 6/1998 | Eggers |
| 5,772,655 | A | 6/1998 | Bauer et al. |
| 5,772,670 | A | 6/1998 | Brosa |
| 5,776,128 | A | 7/1998 | Eggers |
| 5,776,130 | A | 7/1998 | Buysse et al. |

(56) References Cited

U.S. PATENT DOCUMENTS

| | | |
|---|---|---|
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,214,034 B1 * | 4/2001 | Azar ............................. 607/89 |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |

(56) References Cited

U.S. PATENT DOCUMENTS

| | | |
|---|---|---|
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |

(56) References Cited

U.S. PATENT DOCUMENTS

| | | |
|---|---|---|
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| 7,137,980 B2 | 11/2006 | Buysse et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelto, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0015163 A1* | 1/2004 | Buysse et al. .................. 606/34 |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0143263 A1 | 7/2004 | Schechter et al. |
| 2004/0148035 A1 | 7/2004 | Barrett et al. |
| 2004/0162557 A1 | 8/2004 | Tetzlaff et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |

(56) References Cited

U.S. PATENT DOCUMENTS

| | | |
|---|---|---|
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2006/0025760 A1* | 2/2006 | Podhajsky ............... 606/38 |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1* | 7/2007 | Couture et al. ............. 606/39 |
| 2007/0173814 A1 | 7/2007 | Hixson et al. |
| 2007/0179499 A1 | 8/2007 | Garrison |
| 2007/0179571 A1* | 8/2007 | De Taboada ......... A61N 5/0613 607/88 |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1* | 1/2008 | Odom ..................... 606/51 |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0221409 A1* | 9/2008 | Hoarau ............... A61B 5/0075 600/310 |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |
| 2012/0165818 A1* | 6/2012 | Odom ..................... 606/51 |

FOREIGN PATENT DOCUMENTS

| | | |
|---|---|---|
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |

(56) References Cited

FOREIGN PATENT DOCUMENTS

| | | |
|---|---|---|
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1535581 | 6/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1707143 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

(56) References Cited

OTHER PUBLICATIONS

Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.

(56) References Cited

OTHER PUBLICATIONS

International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
European Search Report for EP 09 16 8153 dated Dec. 18, 2009.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.
Examination Report for application No. 09 168 153.6 dated Jul. 29, 2016.

\* cited by examiner

ELECTROSURGICAL INSTRUMENT INCLUDING A SENSOR

CROSS REFERENCE TO RELATED APPLICATION

This application is related to U.S. application Ser. No. 10/427,832, filed on May 1, 2003 by Buysse et al., now U.S. Pat. No. 7,137,980 entitled "Method and system for controlling output of RF medical generator", the entire contents thereof are hereby incorporated by reference in its entirety herein.

BACKGROUND

Technical Field

The present disclosure relates to an electrosurgical system and method and more particularly, the present disclosure relates to an electrosurgical system and method that includes an electrosurgical instrument with a sensor, such as a temperature sensor, a tissue hydration sensor, and an optical clarity sensor.

Description of Related Art

Electrosurgery is the application of electricity and/or electromagnetic energy to cut or modify biological tissue during a surgical procedure. Generally, electrosurgery utilizes an electrosurgical generator, a return electrode, and a source electrode. The electrosurgical generator produces an electromagnetic wave (referred to herein as "electrosurgery energy"), typically above 100 kilohertz, between the return and source electrodes when applied to tissue. The electromagnetic wave created therebetween dissipates energy as heat as it travels from one electrode to the other. Electromagnetic frequencies above 100 kilohertz are employed to avoid muscle and/or nerve stimulation.

During electrosurgery, current generated by the electrosurgical generator is conducted through the patient's tissue disposed between the two electrodes. The current causes the tissue to heat up as the electromagnetic waves overcome the tissue impedance. Although many other variables affect the total heating of the tissue, usually more current density directly correlates to increased heating. Electrosurgical energy is typically used for cutting, dissecting, ablating, coagulating, and/or sealing tissue.

The two basic types of electrosurgery employed are monopolar and bipolar electrosurgery; however, both types use an "active" and a "return" electrode. In bipolar electrosurgery, the surgical instrument has an active electrode and a return electrode on the same instrument or in very close proximity, usually causing current to flow through a smaller amount of tissue. In monopolar electrosurgery, the return electrode is located elsewhere on the patient's body and is usually not part of the electrosurgical instrument itself. In monopolar electrosurgery, the return electrode is part of a device usually referred to as a return pad.

The effectiveness of the application of electrosurgical energy is affected by a variety of factors, including the patient's age, weight, the type of tissue being modified, and the desired tissue effect. Different voltages, currents, duty cycles and frequencies are used to cause a variety of tissue effects. For example, coagulation requires the application of different electrosurgical energy compared to cutting.

Many electrosurgical procedures require cutting or ligating blood vessels or vascular tissue. A surgeon can cauterize, coagulate, desiccate, and/or reduce bleeding by controlling the intensity, frequency and duration of the electrosurgical energy applied to the tissue between the electrodes of the electrosurgical instrument.

The process of coagulating vessels is different from electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

A way to achieve effective operation of the electrosurgical instrument is to monitor the electrosurgical energy directly. Additionally or alternatively, the tissue being acted upon can be monitored. This monitoring can be used in a feedback loop of a control component that controls the generation of the electrosurgical energy.

SUMMARY

The present disclosure relates to an electrosurgical system and method and more particularly, the present disclosure relates to an electrosurgical system and method that includes an electrosurgical instrument with a sensor, such as a temperature sensor, a tissue hydration sensor, and an optical clarity sensor.

In one embodiment of the present disclosure, an electrosurgical system includes an electrosurgical generator, an electrosurgical instrument, an optical clarity sensor and a control component. The electrosurgical generator generates electrosurgical energy for use during electrosurgery. The electrosurgical instrument is coupled to the electrosurgical generator and treats tissue. The optical clarity sensor is coupled to the electrosurgical generator and is adapted to measure tissue with at least two optical frequencies. The control component is operatively coupled to the optical clarity sensor and receives sensor data therefrom. The control component communicates control instructions to the electrosurgical generator to control the generation of the electrosurgical energy.

In another embodiment of the present disclosure, the sensor data includes optical clarity measurements of tissue. The control component instructs the electrosurgical generator to generate the electrosurgical energy corresponding to the optical clarity measurements which corresponds to tissue being less than about 60 degrees Celsius or less than about 100 degrees Celsius.

In another embodiment of the present disclosure, the control component instructs the electrosurgical generator to generate the electrosurgical energy corresponding to at least one optical clarity measurement being in a predetermined range and/or tissue hydration being within a predetermined range. Additionally or alternatively, the control component instructs the electrosurgical generator to generate the electrosurgical energy when the at least one optical clarity measurement falls within a predetermined range.

In another embodiment of the present disclosure, the electrosurgical instrument includes a shaft, a drive assembly, and a movable handle. The shaft has first and second jaw members at a distal end thereof. One or both of the jaw members include an electrode disposed thereon which applies the electrosurgical energy to tissue. One (or both) of the jaw members includes the optical clarity sensor disposed thereon. The drive assembly is operatively coupled to the shaft and moves one of the jaw members relative to the other from a first position to a second position. In the first position, the first jaw member is disposed in spaced relation relative to the second jaw member and in the second position, the first jaw member grasps tissue. The movable handle actuates the drive assembly.

In another embodiment of the present disclosure, the electrosurgical instrument includes first and second shafts having first and second jaw members, respectively. The second shaft is pivotally connected to the first shaft. One (or both) of the jaw members includes an electrode disposed thereon configured to apply the electrosurgical energy to tissue. One of the jaw members includes the optical clarity sensor disposed thereon.

In another embodiment of the present disclosure, one or more of the optical frequencies of the at least two optical frequencies is adapted to be a reference, is adapted to be substantially absorbed by water and/or is adapted such that water is substantially translucent to the optical frequency. The at least two optical frequencies may include first and second optical frequencies such that the first optical frequency is adapted to be substantially absorbed by water and the second optical frequency is adapted such that water is substantially translucent to the second optical frequency. The sensor data may include a first measurement of the first optical frequency and second measurement of the second optical frequency. The electrosurgical generator can compare the first measurement to the second measurement, e.g., such that at least one of tissue hydration, tissue temperature, optical clarity and tissue thickness is determined.

In yet another embodiment of the present disclosure, an electrosurgical generator includes a control component. The control component includes a receiving module, a waveform controller and a control algorithm. The control component is at least partially implemented by an operative set of processor executable instructions configured for execution by at least one processor. The receiving module is operatively connected to a optical clarity sensor and receives sensor data therefrom. The optical clarity sensor is adapted to measure tissue with at least two optical frequencies and the sensor data includes a tissue temperature sensor measurement, a tissue hydration sensor measurement, and/or an optical clarity sensor measurement utilizing the at least two optical frequencies. The waveform controller communicates control instructions to the electrosurgical generator to control the generation of electrosurgical energy. The control algorithm is in operative communication with the receiving module and the waveform controller. The control algorithm processes the data to calculate the control instructions and communicates the control instructions to the waveform controller.

The control algorithm may be a proportional-integral-derivative control algorithm. The control module may include one or more microcontrollers to execute the operative set of processor executable instructions. The receiving module may include an analog to digital conversion circuit configured to convert the data from an analog signal to a digital signal and/or the waveform controller includes a digital-to-analog conversion circuit configured to convert the control instructions from a digital signal to an analog signal. The waveform controller may includes an electronic signal amplifier configured to amplify the analog signal of the control instructions such that the amplified analog signal instructs the electrosurgical generator.

In another embodiment of the present disclosure, a method for controlling generation of electrosurgical energy includes: providing an electrosurgical system; activating an optical clarity sensor of the electrosurgical system to communicate with the control component; and monitoring sensor data from the optical clarity sensor.

BRIEF DESCRIPTION OF THE DRAWINGS

These and other advantages will become more apparent from the following detailed description of the various embodiments of the present disclosure with reference to the drawings wherein.

DETAILED DESCRIPTION

Figure 1:
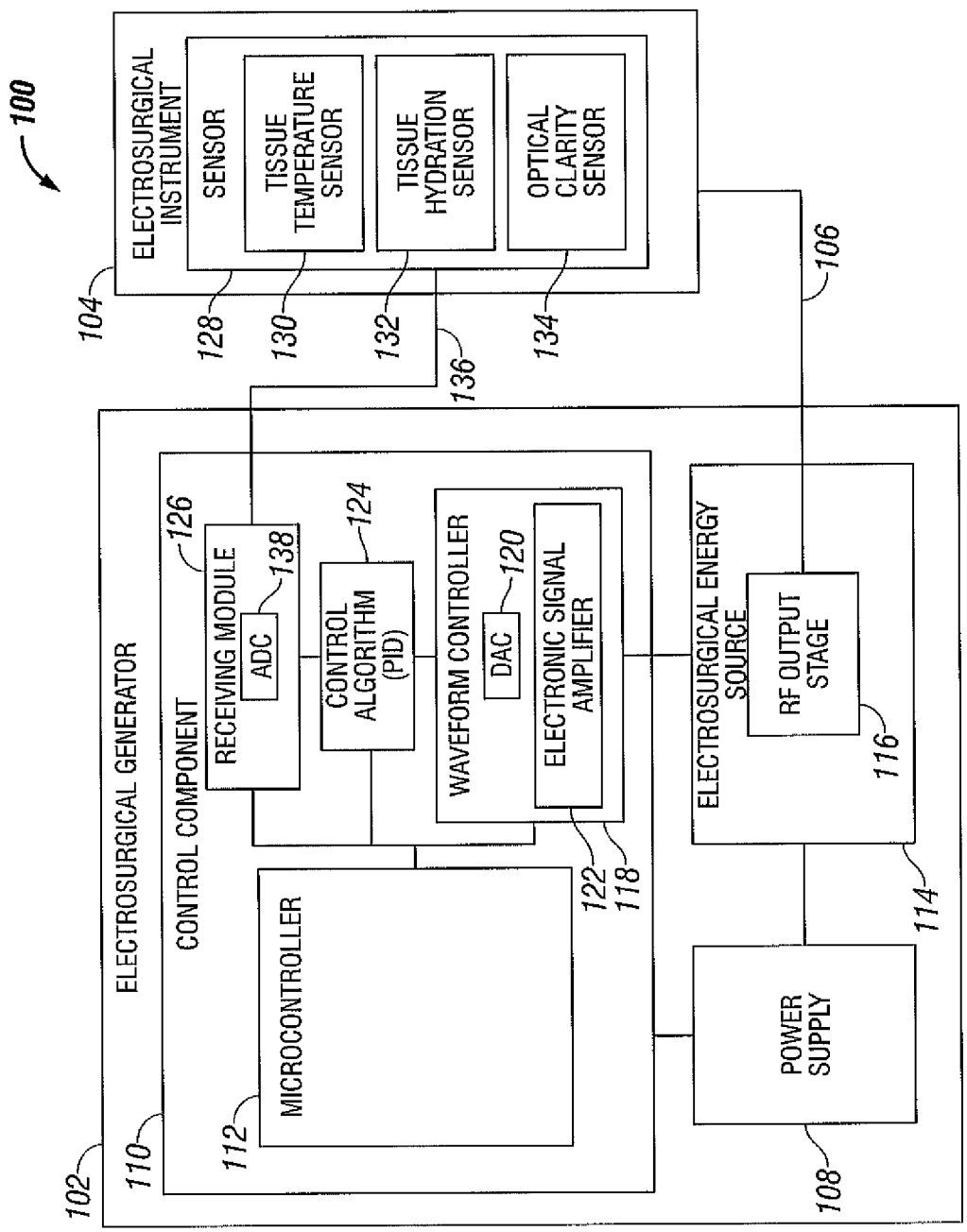
FIG. 1 is a schematic block diagram of an electrosurgical system that includes an electrosurgical instrument with a sensor according to the present disclosure.

Referring to the drawings, FIG. 1 is a block diagram depicting an electrosurgical system 100. Electrosurgical system 100 includes electrosurgical generator 102 that generates electrosurgical energy. The electrosurgical energy is used to perform electrosurgery on a patient using electrosurgical instrument 104.

Electrosurgical generator 102 may have several user interface devices (e.g., touch screens, switches, dials, and the like) to assist a surgeon to achieve the desired results. The surgeon can use the user interface devices to input various data parameters into electrosurgical generator 102. However, not all factors can be known and/or are readily known to the surgeon. For example, the specific physiology of patient P (e.g., age, weight, electrolyte density, PH, osmolarity, fluid volume and pressure, diseases and the like), temperature, humidity, and other factors that may influence electrosurgery, may not be readily know to the surgeon.

Thus, to better assist in ensuring an effective electrosurgical procedure, electrosurgical generator 102 may use several techniques to adjust the applied electrosurgical energy. Some such techniques include calculating or monitoring the tissue impedance, current, voltage, duty cycle, tissue resistance and the like. Electrosurgical generator 102 can use these calculated or monitored properties to make adjustments to the electrosurgical energy applied to tissue by electrosurgical instrument 104. Additionally or alternatively, as is discussed in more detail below, feedback data may be provided to electrosurgical generator 102 by electrosurgical instrument 104.

Electrosurgical instrument 104 can be a monopolar electrosurgical instrument or a bipolar electrosurgical instrument. For example, electrosurgical instrument 104 may be forceps, a vessel sealing electrosurgical instrument, a cutting electrosurgical instrument, or the like. The electrosurgical energy generated by electrosurgical generator 102 is transferred to electrosurgical instrument 104 via cable 106. Cable 106 includes an active path and a return path. The active and/or return paths may be made out of a sufficiently conductive material having an appropriate geometry. For example, cable 106 may be a coaxial cable having a geometry that mitigates attenuation losses within the frequency range of the electrosurgical energy.

Electrosurgical generator 102 may be powered by Alternating Current or Direct Current (referred to herein as "AC" and "DC", respectively); however, it is preferable that electrosurgical generator 102 is powered by a power source via a standardized receptacle outlet, e.g., a 110 volt outlet as typically found within the United States. Although electrosurgical generator 102 is connected to an external power source, power supply 108 conditions and converts the external power source (e.g., AC power from an outlet) to sufficiently power various parts of electrosurgical generator 102.

For example, consider that control component 110 includes microcontroller 112; microcontrollers typically need a DC power source, such as a 5-Volt DC power source. Thus, power supply 108 can also include circuitry to ensure that microcontroller 112 is sufficiently powered, e.g., circuitry that includes transformers, rectifiers, capacitors, voltage regulators, or the like. Additionally, power supply 104 supplies power to control component 110 and electrosurgical energy source 114.

Electrosurgical energy source 114 includes circuitry sufficient to translate instructions from waveform controller 118 from one form to another form more conducive for interpretation by RF output stage 116. RF output stage 116 includes circuitry to safely and efficiently transfer the electrosurgical energy to electrosurgical instrument 104. For example, RF output stage 116 may include an output transformer providing an isolated ground, an output amplifier, impedance matching circuitry to facilitate efficient power transfer, or the like, while electrosurgical energy source 114 may include a variable output power supply connection, voltage scaling circuitry, a buffer such as a voltage follower, or the like.

RF output stage 116 may be connected to cable 106 using an RF connector, such as an coaxial cable female connector, facilitating low attenuation injection of the electrosurgical energy into cable 106. Also, electrosurgical energy source 114 implements the instructions received from waveform controller 118 while ensuring that RF output stage 116 properly complies with the instructions. For example, waveform controller 118 may send multiple signals regarding the desired characteristics of the electrosurgical energy to be injected into cable 106, and electrosurgical energy source 114 translates those signals to ensure that RF output stage 116 complies with the instructions by comparing a voltage sense to an RF drive (not depicted in FIG. 1). Additionally or alternatively, electrosurgical energy source 114 may include safety and/or isolation circuitry.

Electrosurgical component 102 also includes control component 110. Control component 110 may be implemented in hardware, software, firmware, or some combination thereof, and includes waveform controller 118, control algorithm 124, and receiving module 126. For example, control algorithm 124 may be implemented in software processed by microcontroller 112.

Waveform controller 118 instructs electrosurgical energy source 114 to maintain a particular amplitude, voltage, current, frequency, duty cycle, and/or other properties of the electrosurgical energy for application to tissue. Waveform controller 118 includes a digital to analog converter (referred to herein as a "DAC") 120 and electronic signal amplifier 122. Additionally or alternatively, waveform controller 118 may include output relays, scaling relays, and/or an output waveform microcontroller (not depicted). Waveform controller 118 can also instruct the electrosurgical energy source 114 using an analog or a digital signal. For example, waveform controller 118 may have a digital waveform stored therein for converting the waveform to analog form via DAC 120. Electrosurgical signal amplifier 112 may amplify the analog waveform by a scalar value, e.g., 10, before sending the waveform to electrosurgical energy source 114.

However, control component 110 determines what properties the electrosurgical energy should have based upon sensor data, specifically, control component 110 can form a feed-back loop with sensor 128. Sensor 128 may include tissue temperature sensor 130, tissue hydration sensor 132, and/or optical clarity sensor 134. The sensor data is received by receiving module 126 via cable 136. The sensor data may be in analog or digital form. Additionally or alternatively, the sensor data may be converted from analog to digital form via analog to digital converter (referred to herein as "ADC") 138.

The sensor data is processed by control algorithm 124 to calculate the control instructions. The calculated control instructions are communicated to waveform controller 118. Control algorithm 124 may be a proportional-integral-derivative control algorithm and/or some other control algorithm to facilitate application of the electrosurgical energy to achieve the desired tissue effect.

Figure 2A:
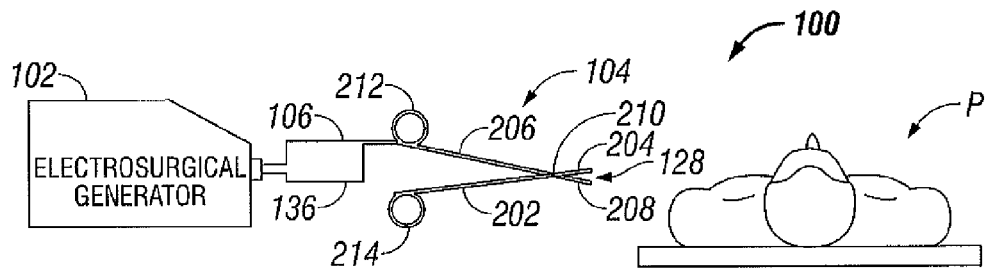
FIGS. 2A-2B are schematic block diagrams of an electrosurgical system according to the present disclosure.
Figure 2B:
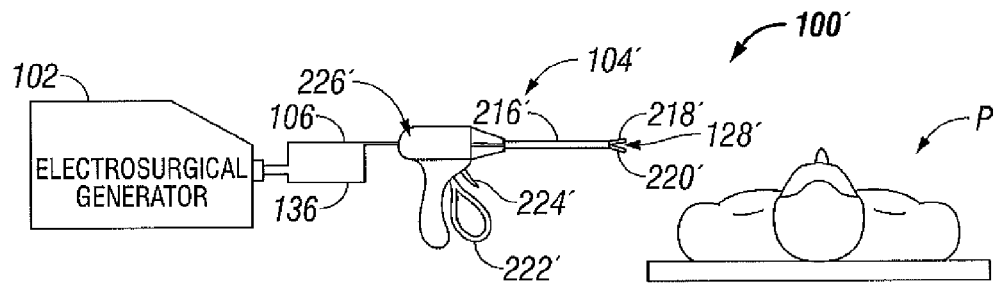

Referring simultaneously to FIGS. 1, 2A, and 2B, sensor 128 may be located on electrosurgical instrument 104 and is shown in two embodiments by FIGS. 2A and 2B. Electrosurgical instrument 104 may include an active and/or a return electrode, and sensor 128 may be disposed on or near at least one of the electrodes, or otherwise positioned to take at least one tissue measurement of Patient P of FIGS. 2A and 2B. Cable 106 may include an active path and a return path for apply electrosurgical energy to patient P while electrosurgical generator 102 receives sensor data through cable 136.

Referring to the drawings, FIG. 2A shows an open electrosurgical instrument 104 that includes shaft 202 with jaw member 204 on the end. Electrosurgical instrument 104 also includes shaft 206 with jaw member 208 on the end as well. Shaft 206 is attached to shaft 202 via pivot 210 making them pivotally connected. Pivot 210 may be formed from pins, bearings, axels, or the like to assist in the movement of jaws 204 and 208 relative to each other. Grips 212 and 214 move shafts 206 and 202, respectively, allowing a surgeon to grip and/or compress tissue of patient P between jaw members 204 and 208. For example, a surgeon may apply pressure to force grips 212 and 214 together when a vessel is positioned between jaw members 204 and 208, gripping the vessel. Electrosurgical energy may then be applied between jaw members 204 and 208 by electrodes, sealing the vessel. Sensor 128 may be used by electrosurgical generator 102 to assist in the vessel sealing (discussed in more detail below). Further details relating to open instrument vessel sealing are discussed in commonly-owned U.S. application Ser. No. 10/962,116.

Referring now to FIG. 2B, another embodiment is shown of electrosurgical system 100 for use with an electrosurgical instrument 104'. Electrosurgical instrument 104' includes a shaft 216' that has a distal end that includes jaw members 218' and 220'. Within electrosurgical instrument 104', a drive assembly (not shown) actuates jaw members 219' and 220' so that initially they are spaced by a distance, and, when actuated, move relative to each other. Actuation assembly includes handle 220' that when "squeezed" causes jaw members 218' and 220' to move closer together pivotally, approximately pivoting along their attachment point to the distal end of shaft 216'. Trigger 226' causes the electrosurgical generator 102 to apply the electrosurgical energy. Jaw members 220' and 218' may each have an active and/or a return electrode. Sensor 128 may be disposed on or near one of the electrodes. Additionally or alternatively, sensor 128 can be positioned to take at least one measurement of tissue of patient P and send the measurement to electrosurgical generator via cable 136.

Referring again to FIG. 1, as mentioned previously, sensor 128 may include tissue temperature sensor 130, tissue hydration sensor 132, and optical clarity sensor 134, and can communicate data through cable 136 to electrosurgical generator 102; the data may include a tissue temperature measurement, a tissue hydration measurement, and an optical clarity measurement of tissue.

Tissue temperature sensor 130 can measure tissue temperature and communicate one or more tissue temperature measurements to electrosurgical generator 102. The biology of tissue is highly sensitive to temperature. For example, above 60 degrees Celsius, collagen protein denatures causing the tissue bond strength to be reduced. Above 100 degrees Celsius, the water within the cell vaporizes leading to cell destruction. Electrosurgical generator 102 can monitor the tissue temperature via temperature measurements received by receiving module 126 through cable 136, and adjust the electrosurgical energy based upon the received measurements to achieve a desired result, e.g., by keeping the tissue temperature measurements below a value, above a value, and/or within a predetermined range.

For example, for tissue cutting, it may be desirable to generate electrosurgical energy to ensure that the tissue is above about 100 degrees Celsius. In other applications, such as vessel sealing, it is more desirable to maintain a tissue temperature of less than about 60 degrees Celsius. Also, a predetermined range may be used to ensure that the temperature is high enough to cause tissue fusion but low enough to prevent loss of tissue strength. Programming of the tissue temperature desired (or range desired) may be preprogrammed within electrosurgical generator 102, or may manually be set by the operator.

Tissue temperature sensor 130 may include a contact or a non-contact temperature sensor. Tissue temperature sensor 130 also include a ratio or optical pyrometer, a thermal imager temperature sensor, fiber optic based temperature sensor, thermocouples, thermistors, resistance temperature detector ("RTD"), semiconductor, or the like to measure temperature. Note that cable 136 may include one or more conductive cable paths (i.e., wires) and/or may include a fiber optic cable path (also referred to herein as a "fiber optic cable"). Additionally or alternatively, sensor 128 may include additional components or circuitry to aide in the communication of measurements to electrosurgical generator 102. For example, electrosurgical generator 102 may provide power to circuitry within sensor 128 via cable 136 to enable the circuitry to communicate measurements to electrosurgical generator 102 using a pulsed width modulation based communication technique. Also, cable 106 may be bundled with cable 136 (not depicted).

Tissue hydration sensor 132 can communicate to electrosurgical generator 102 a tissue hydration measurement of some tissue of patient P (see FIGS. 2A and 2B). For example, tissue hydration sensor 132 can approximate tissue hydration of the tissue between jaw members 204 and 208 of FIG. 2A, and/or between jaw members 218' and 220' of FIG. 2B. The measurement of the tissue hydration may be accomplished using an optical based sensor, electrical based sensor, or other sufficient tissue hydration sensor. As tissue is heated the water therein may evaporate slowly. The tissue hydration sensor 132 may measure this decreasing tissue hydration and communicate a series of tissue hydration measurements to receiving module 126 via cable 136. Control Algorithm 126 may instruct waveform controller 118 to continue to apply the electrosurgical energy until the tissue hydration sensor 132 falls within a predetermined threshold.

For example, during electrosurgery a surgeon may use surgical instrument 216 of FIG. 2A to clamp onto a vessel between jaw members 204 and 208. The surgeon may then activate the electrosurgical energy (e.g., by a foot pedal) to start the vessel sealing. The initial tissue hydration measurement of tissue hydration sensor 132 may be, for exemplary purposes only, about 60% water content, and control algorithm 124 may have a predetermined threshold of 30% water content. As the electrosurgical energy is applied, consecutive tissue hydration measurements measured by tissue hydration sensor 132 measures the reducing water content and instructs waveform controller 118 to continue to apply the electrosurgical energy until control algorithm 124 detects an approximate 30% water content tissue hydration measurement. When the 30% water content tissue hydration measurement is detected, control algorithm 124 may instruct waveform controller 118 to stop applying electrosurgical energy to electrosurgical instrument 104. An alarm and/or an indicator may indicate to the surgeon that the vessel is sealed.

Referring simultaneously to FIGS. 1, 2A, and 2B, sensor 128 includes optical clarity sensor 134. Optical clarity sensor 134 may use optical frequencies which may be visible or outside of visual perception to make an optical clarity measurement.

Referring to FIG. 2A, an optical source may inject photons from jaw member 204 through tissue and to jaw member 208 where an absorption and/or transparency measurement can be made. Jaw member 204 may include an LED, a laser, a fiber optical coupling lens, or the like. Additionally or alternatively, cable 136 may include a fiber optic cable that carries light from electrosurgical generator 102 that is focused to travel from jaw member 204 thorough tissue and to jaw member 208. Jaw member 208 may include a fiber optic coupling lens to gather the photons and carry them back to electrosurgical generator 102 through a fiber optic cable located within cable 136.

For example, electrosurgical generator 102 may include a semiconductor based laser that injects photons into a fiber optic cable within cable 136. The photons travel down the core of the fiber optic cable to jaw member 204, where a lens injects the photons into tissue contained within jaw members 204 and 208. Jaw member 208, in this example, contains a lens that couples the photons back into a fiber optic cable that carries the photons to electrosurgical generator 102. Receiving module 126 may include photodetector that measures the amount of photons that are received, and converts received photons into an electronic signal. Referring to FIG. 2B, jaw members 218' and 220' may behave similarly to the jaw members 204 and 208 of FIG. 2A, with regards to optical clarity sensor 134.

Optical clarity sensor 134 may utilize a broadband optical wavelength that has a relatively large bandwidth, e.g., a wavelength produced by a LED source. Additionally or alternatively, optical clarity sensor 134 may utilize several optical wavelengths to measure wavelength-dependent optical clarity of the tissue.

For example, optical clarity sensor 134 may use a first wavelength that is more readily absorbed by water than by other molecules found within the tissue, and a second wavelength that is more readily absorbed by a particular protein found throughout human tissue. When the electrosurgical energy is applied to the tissue, the absorption characteristics of the two wavelengths may be compared. If a surgeon is applying too much pressure to the tissue causing the tissue to be "squeezed out" of the jaw members, both wavelengths should have an increase in optical transmissibility because the tissue is "thinning" between the jaw members. However, if only the first wavelength (the one that is more readily absorbed by the water) has an increase of optical transmissibility while the second wavelength maintains its optical transmissibility measurement, the reasons for the changes to the optical transmissibility of the first wavelength is more likely to be due to the evaporation of water. Therefore, optical clarity sensor 134 may use multiple optical wavelengths to communicate an optical clarity sensor measurement to electrosurgical generator 102 to measure wavelength-dependent optical clarity, e.g., by using wave division multiplexing.

Figure 3:
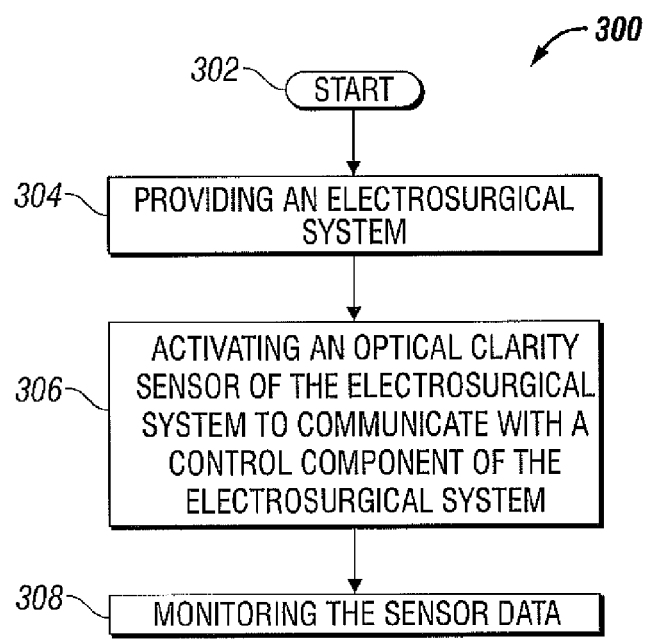
FIG. 3 is a flow chart diagram illustrating a method for using an electrosurgical system that includes an electrosurgical instrument with a sensor according to the present disclosure.

Referring to the drawings, FIG. 3 is a flow chart diagram illustrating a method 300 for using an electrosurgical system that includes an electrosurgical instrument with a sensor. Method 300 starts at step 302 and includes providing an electrosurgical system 304. The electrosurgical system of step 302 may be electrosurgical system 100 as shown in FIGS. 1, 2A, 2B, a monopolar electrosurgical system, or a bipolar electrosurgical system. The electrosurgical system of step 304 includes an optical clarity sensor and a control component. Method 300 further includes step 306 which is activating the optical clarity sensor of the electrosurgical system (of step 304) to communicate with a control component of the electrosurgical system (of step 304). The sensor of step 306 may be sensor 128 of FIG. 1 and includes optical clarity sensor 134. Also, the control component may be control component 110 of FIG. 1. Additionally, method 300 includes monitoring the sensor data 308. The sensor data of step 308 may be communicated via cable 136 to control component 110, that is received by receiving module 126 of FIG. 1.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   an electrosurgical generator configured to generate electrosurgical energy for use during electrosurgery;
   an electrosurgical instrument operatively coupled to the electrosurgical generator and configured to treat tissue;
   a light source operatively coupled to the electrosurgical generator, the light source configured to transmit light through a first side of the tissue;
   an optical clarity sensor operatively coupled to the electrosurgical generator and configured to detect light from the light source transmitted through the tissue at a second, opposing side of the tissue, wherein the optical clarity sensor is adapted to measure the light transmitted through the tissue at at least two optical frequencies, wherein the light at a first optical frequency of the at least two optical frequencies is readily absorbed by water and the light at a second optical frequency of the at least two optical frequencies is readily absorbed by protein found in tissue; and
   a control component operatively coupled to the optical clarity sensor configured to receive sensor data therefrom, wherein the control component is configured to compare absorption characteristics of the tissue at the at least two optical frequencies and communicate control instructions to the electrosurgical generator to control the generation of the electrosurgical energy.

2. An electrosurgical system according to claim 1, wherein the sensor data includes at least one optical clarity measurement of tissue, wherein the control component is configured to instruct the electrosurgical generator to generate the electrosurgical energy corresponding to the at least one optical clarity measurement corresponding to tissue being less than about 60 degrees Celsius.

3. An electrosurgical system according to claim 1, wherein the sensor data includes at least one optical clarity measurement of tissue, wherein the control component is configured to instruct the electrosurgical generator to generate the electrosurgical energy corresponding to the at least one optical clarity measurement being less than about 100 degrees Celsius.

4. An electrosurgical system according to claim 1, wherein the sensor data includes at least one optical clarity measurement of tissue, wherein the control component is configured to instruct the electrosurgical generator to generate the electrosurgical energy corresponding to the at least one optical clarity measurement being in a predetermined range.

5. An electrosurgical system according to claim 1, wherein the sensor data includes at least one optical clarity measurement of tissue, wherein the control component is configured to instruct the electrosurgical generator to generate the electrosurgical energy when the at least one optical clarity measurement corresponds to tissue hydration being within a predetermined range.

6. An electrosurgical system according to claim 1, wherein the electrosurgical instrument includes:
   a shaft having a first jaw member and a second jaw member at a distal end thereof, at least one of said jaw members including an electrode disposed thereon configured to apply the electrosurgical energy to tissue, wherein at least one of the jaw members includes the optical clarity sensor disposed thereon and the other jaw member includes the light source disposed thereon;
   a drive assembly operatively coupled to the shaft which is positionable to move at least one of the first jaw member or second jaw member relative to the other from a first position wherein the first jaw member is disposed in spaced relation relative to the second jaw member to a second position wherein the first and second jaw members are configured to grasp tissue; and
   a movable handle which actuates the drive assembly.

7. An electrosurgical system according to claim 1, wherein the electrosurgical instrument includes:
   a first shaft having a first jaw member; and
   a second shaft having a second jaw member, wherein the second shaft is pivotally connected to the first shaft, at least one of said jaw members includes an electrode disposed thereon configured to apply the electrosurgical energy to tissue, at least one of the jaw members includes the optical clarity sensor disposed thereon.

8. The electrosurgical system according to claim 1, wherein an optical frequency of the at least two optical frequencies is a reference frequency.

9. The electrosurgical system according to claim 1, wherein an optical frequency of the at least two optical frequencies is adapted such that water is substantially translucent to the optical frequency.

10. The electrosurgical system according to claim 1, wherein the light at the first optical frequency of the at least two optical frequencies is adapted to be substantially absorbed by water and the light at the second optical frequency of the at least two optical frequencies is adapted such that water is substantially translucent to the second optical frequency.

11. The electrosurgical system according to claim 10, wherein the sensor data includes a first measurement of the first optical frequency and a second measurement of the second optical frequency, wherein the electrosurgical generator is configured to compare the first measurement to the second measurement.

12. The electrosurgical system according to claim 10, wherein the sensor data includes a first measurement of the first optical frequency and a second measurement of the second optical frequency, wherein the electrosurgical generator is configured to compare the first measurement to the second measurement such that at least one of tissue hydration, tissue temperature, optical clarity and tissue thickness is determined.

\* \* \* \* \*